US006339326B1

(12) United States Patent
Trantow

(10) Patent No.: US 6,339,326 B1
(45) Date of Patent: Jan. 15, 2002

(54) EDDY CURRENT INSPECTION PROBE

(75) Inventor: Richard L. Trantow, Cincinnati, OH (US)

(73) Assignee: General Electric Company, Cincinnati, OH (US)

( * ) Notice: Subject to any disclaimer, the term of this patent is extended or adjusted under 35 U.S.C. 154(b) by 0 days.

(21) Appl. No.: 09/563,041

(22) Filed: May 1, 2000

Related U.S. Application Data

(60) Provisional application No. 60/189,368, filed on Mar. 15, 2000.

(51) Int. Cl.[7] ........................ G01R 33/12; G01N 27/72
(52) U.S. Cl. ..................................... 324/219; 324/238
(58) Field of Search ................................ 324/219, 220, 324/236, 237, 238, 239, 240, 241, 242, 243, 262

(56) References Cited

U.S. PATENT DOCUMENTS

| | | | |
|---|---|---|---|
| 4,196,048 A | 4/1980 | Qurnell et al. ............. 294/86 A |
| 5,315,234 A | 5/1994 | Sutton, Jr. et al. ........... 324/242 |
| 5,329,230 A | 7/1994 | Viertl et al. ................ 324/262 |
| 5,345,514 A | 9/1994 | Mahdavieh et al. ........... 382/8 |
| 5,371,462 A | 12/1994 | Hedengren et al. .......... 324/225 |
| 5,442,286 A | 8/1995 | Sutton, Jr. et al. ........... 324/242 |
| 5,510,709 A | 4/1996 | Hurley et al. ............... 324/242 |
| 5,659,248 A | 8/1997 | Hedengren et al. .......... 324/242 |
| 5,710,378 A | 1/1998 | Dykes et al. ................. 73/601 |
| 5,903,147 A | 5/1999 | Granger, Jr. et al. ........ 324/219 |

Primary Examiner—Walter Snow
(74) Attorney, Agent, or Firm—Andrew C. Hess; V. Ramaswamy

(57) ABSTRACT

An eddy current inspection probe for inspecting a preselected surface at least partially defining an opening in a component. The eddy current inspection probe includes a core moveable between a retracted position and an expanded position in which the probe is sized and shaped for at least partially filling the opening and contacting the preselected surface for inspecting the surface. The probe includes a compliant covering positioned over the exterior surface of the core and an eddy current array positioned over the outer face of the covering. Further, the probe includes an element positioned between an exterior surface of the core and an inner face of the covering having a coefficient of friction selected to permit the inner face of the covering to move tangentially with respect to the exterior surface of the core as the core is moved from the retracted position to the expanded position to ensure intimate contact between probe and the preselected surface of the component being inspected.

9 Claims, 5 Drawing Sheets

EDDY CURRENT INSPECTION PROBE

CROSS REFERENCE TO RELATED APPLICATION

This application claims the benefit of U.S. Provisional Application No. 60/189,368, filed Mar. 15, 2000.

The United States government has rights in this invention under Contract No. N00019-96-C-0080 awarded by the Department of the Navy.

BACKGROUND OF THE INVENTION

The present invention relates generally to eddy current inspection probes for inspecting a surface of a manufactured component, and more particularly to a probe having an improved fit with the surface of the component.

Eddy current inspection is commonly used to detect flaws in surfaces of manufactured components such as gas turbine engine components. During this type of inspection, electromagnetic induction is used to induce eddy currents in the component being inspected. An array of coils inside an eddy current probe generates alternating magnetic fields which induce the eddy currents in the component when the probe is moved near the component. When flaws are present in the component, the flow of eddy currents is altered. The altered eddy currents produce changes in a secondary magnetic field which are detected by the array of coils inside the eddy current probe. The array generates an electrical signal in response to the altered secondary magnetic field. The amplitude of the electrical signal is generally proportionate to the size of the flaw. Thus, approximate sizes and general locations of flaws may be determined using eddy current probes.

The array must be kept at a constant distance from the surface of the component being inspected to ensure the amplitude of the electrical signal is proportionate to flaw size. One way of ensuring a constant distance is by sizing and shaping the probe substantially identically to the feature being inspected. For instance, if the surface of an opening in a gas turbine engine disk such as a dovetail slot bottom is being inspected, a probe sized and shaped substantially identically to the opening is used.

Frequently, the probe is made to collapse so it can fit into the opening. These collapsible probes generally have an expandable core inside a flexible covering which holds the array. In the past, the covering was bonded to the core. As a result, the covering stretched and distorted as it expanded. Changes in the probe shape prevented the array from being positioned at a uniform distance from the surface being inspected. Further, due to variations in size and shape of the actual features being inspected, gaps sometimes occurred between the probe and the surface which also prevented the array from being positioned at a uniform distance from the surface being inspected.

SUMMARY OF THE INVENTION

Among the several features of the present invention may be noted the provision of an eddy current inspection probe for inspecting a preselected surface at least partially defining an opening in a component. The eddy current inspection probe comprises a core having an exterior surface sized and shaped for receipt within the opening of the component. The core is moveable between a retracted position for inserting the probe into and removing the probe from the opening in the component and an expanded position in which the probe is sized and shaped for at least partially filling the opening and contacting the preselected surface of the component for inspecting the surface. In addition, the probe includes a compliant covering positioned over the exterior surface of the core having an inner face facing the core and an outer face opposite the inner face. The probe also comprises an eddy current array positioned over the outer face of the covering for generating and detecting magnetic fields in the component to inspect the preselected surface of the component. The eddy current array has an outer surface shaped substantially identically to the preselected surface of the component when the core is in the expanded position for maintaining the outer surface of the array a preselected distance from the surface of the component. In addition, the probe includes an element positioned between the exterior surface of the core and the inner face of the covering having a coefficient of friction selected to permit the inner face of the covering to move tangentially with respect to the exterior surface of the core as the core is moved from the retracted position to the expanded position to ensure intimate contact between the probe and the preselected surface of the component being inspected.

In another aspect of the present invention, the outer face of the covering has a central portion and opposite end portions extending longitudinally outward from the central portion and the eddy current array is positioned over the central portion of the outer face of the covering. Further, the probe includes a layered element positioned between the exterior surface of the core and the inner face of the covering. The element has a central portion underlying the central portion of the cover and opposite end portions extending longitudinally outward from the central portion of the element and underlying the respective end portions of the covering. The central portion of the element has a first thickness and each of the end portions of the element has a second thickness less than the first thickness so the central portion of the outer face of the covering and the array are raised above the end portions of the outer face of the covering for easing insertion of the central portion of the covering and the array into the opening and ensuring intimate contact between the probe and the preselected surface of the component being inspected.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
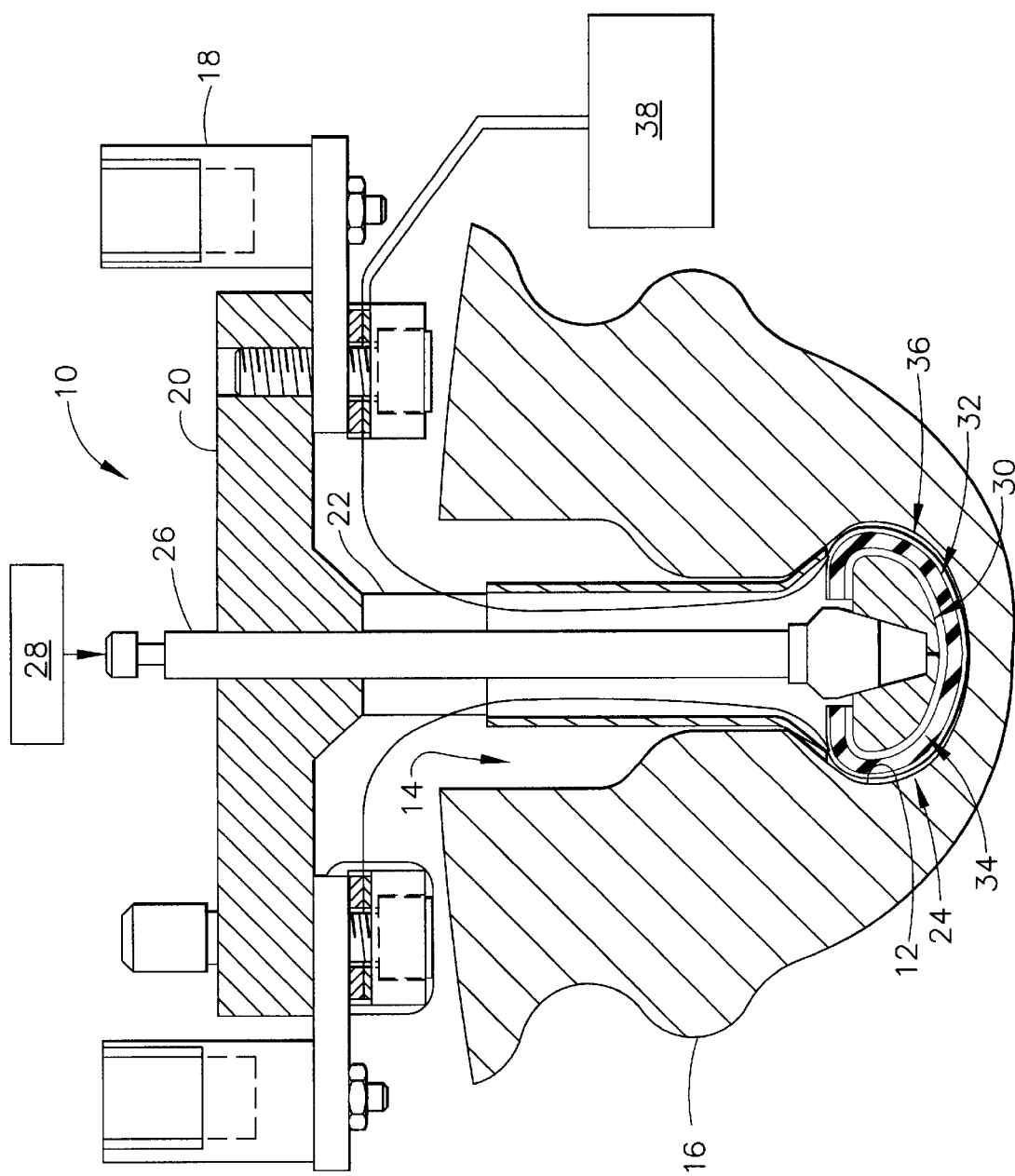
FIG. 1 is a vertical cross section of an eddy current inspection probe of the present invention shown in an opening of a component.

Referring now to the drawings and in particular to FIG. 1, an eddy current inspection probe of the present invention is designated in its entirety by the reference number 10. The probe 10 is sized and shaped for inspecting a preselected surface 12 (e.g., a dovetail slot bottom of a gas turbine engine disk) at least partially defining an opening, generally designated by 14, in a component 16 (partially shown in FIG. 1). The probe 10 is mounted on a conventional fixture 18 positioned adjacent the component 16 to be inspected.

Figure 2:
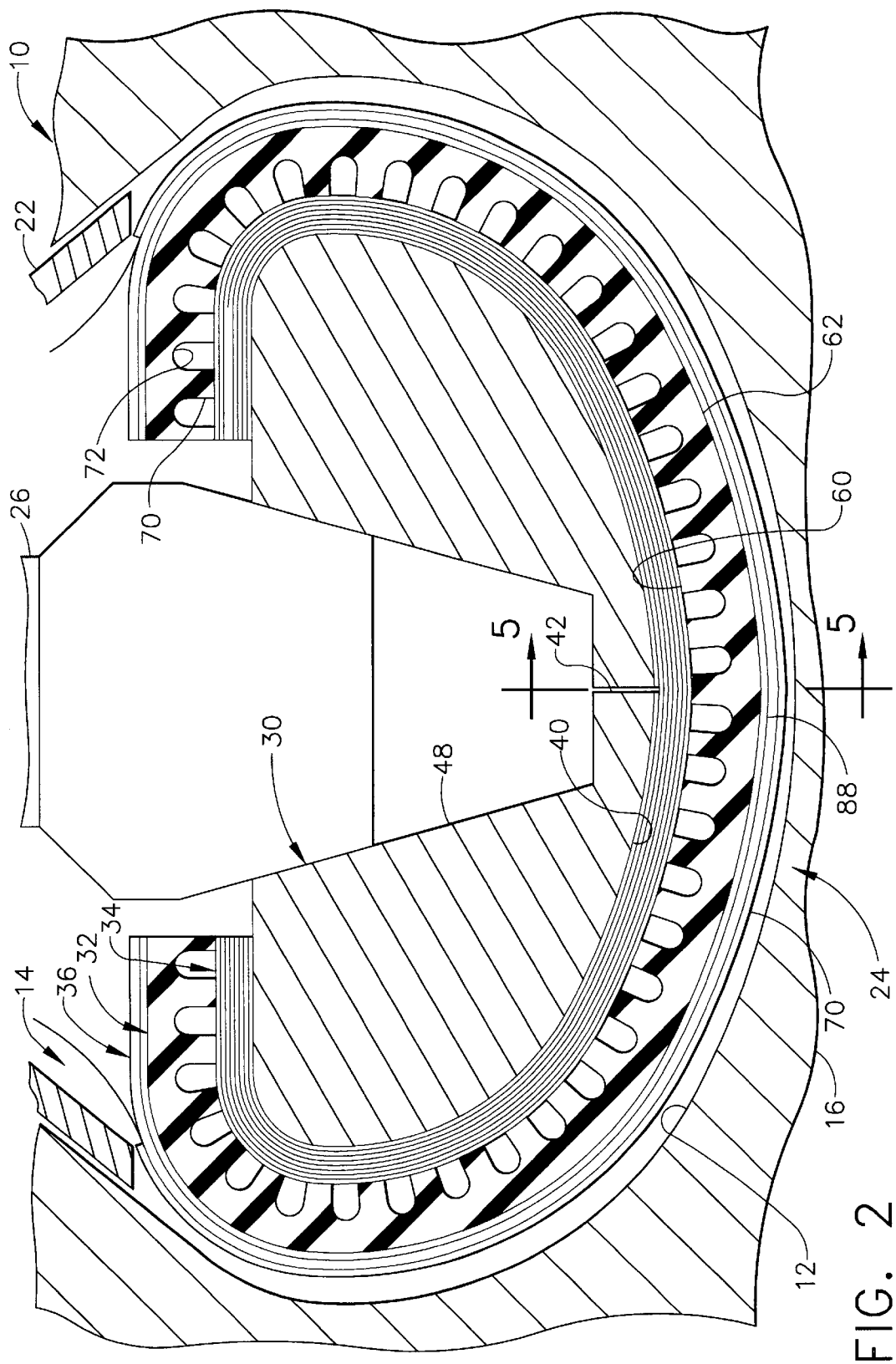
FIG. 2 is a detail of the probe and component showing the probe in a contracted position.
Figure 3:
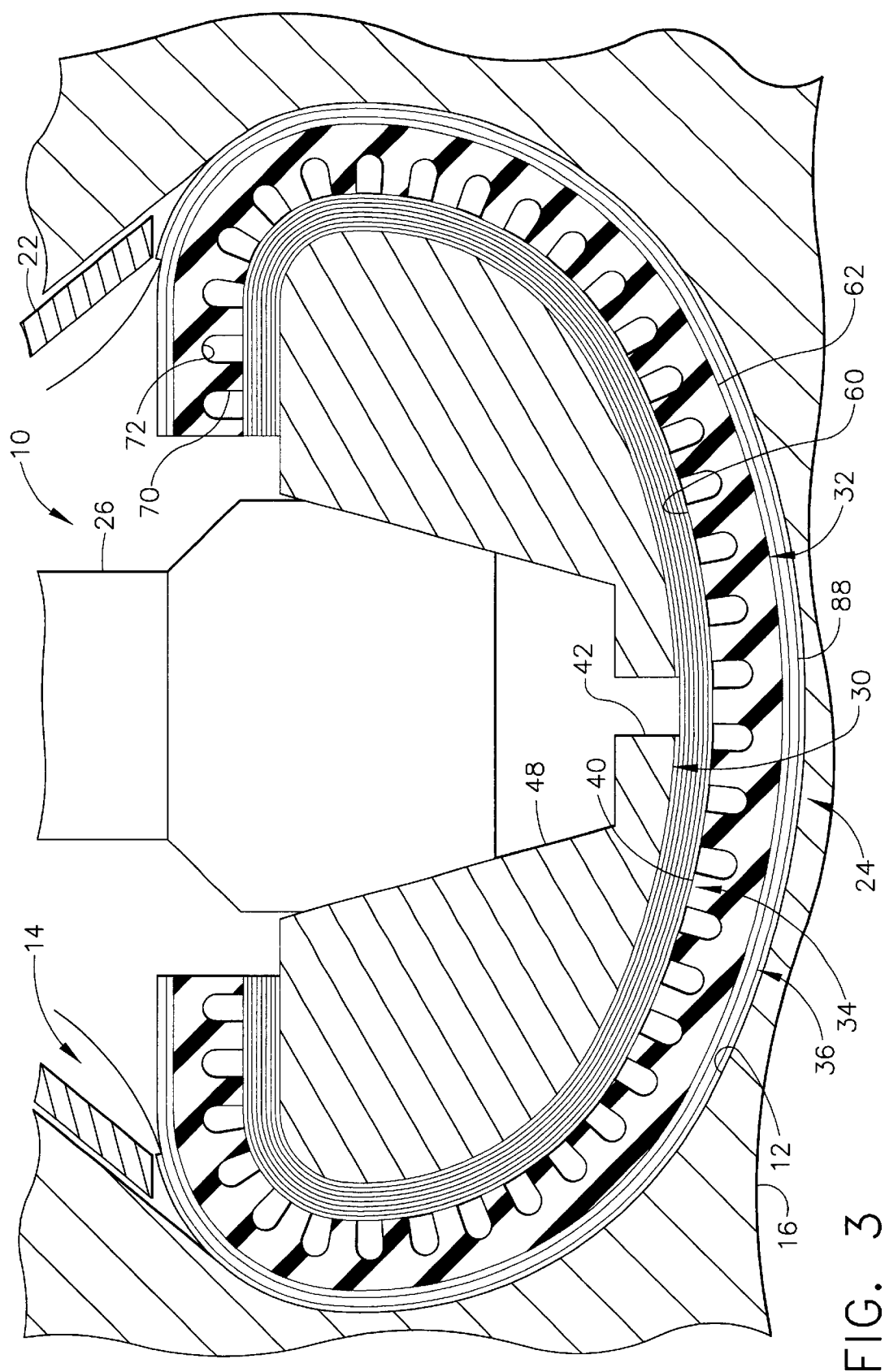
FIG. 3 is a detail similar to FIG. 2 showing the probe in an expanded position.

The probe 10 generally comprises a base 20 which is mounted on the fixture 18, a support 22 extending downward from the base, a head (generally designated by 24) and an actuation rod 26 extending downward through the support. The rod 26 is operatively connected to a conventional actuator 28 for moving the head 24 between a retracted position as shown in FIG. 2 and an expanded position as shown in FIG. 3. As illustrated in FIG. 2, the head 24 comprises a core (generally designated by 30), a compliant covering (generally designated by 32), a layered element (generally designated by 34) positioned between the core and the covering, and an eddy current array (generally designated by 36). As shown in FIG. 1, the eddy current array 36 is connected to a conventional eddy current instrument 38 for providing an output related to flaw size in the surface 12 of the component 16.

Figure 4:
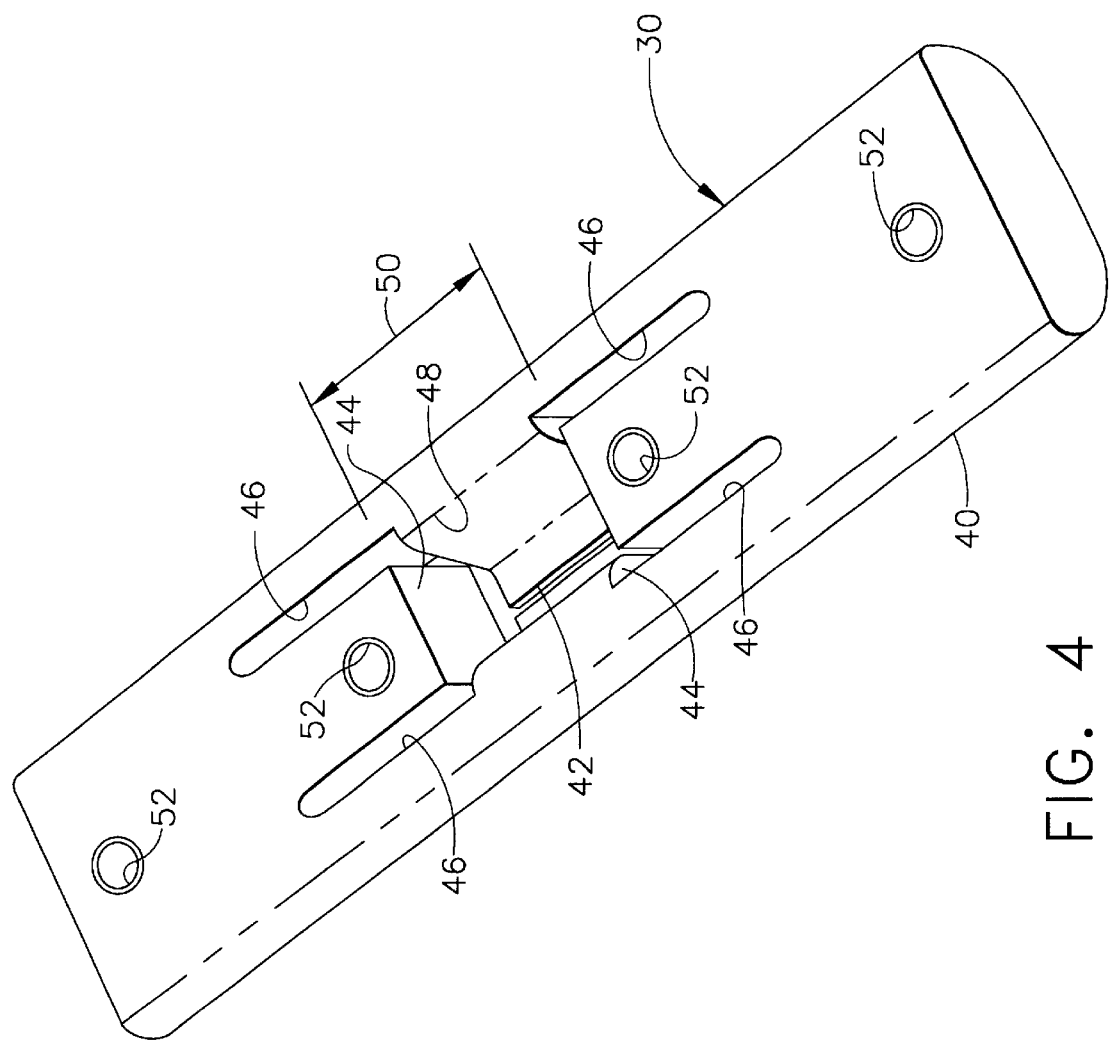
FIG. 4 is a perspective of a core of the probe.
Figure 5:
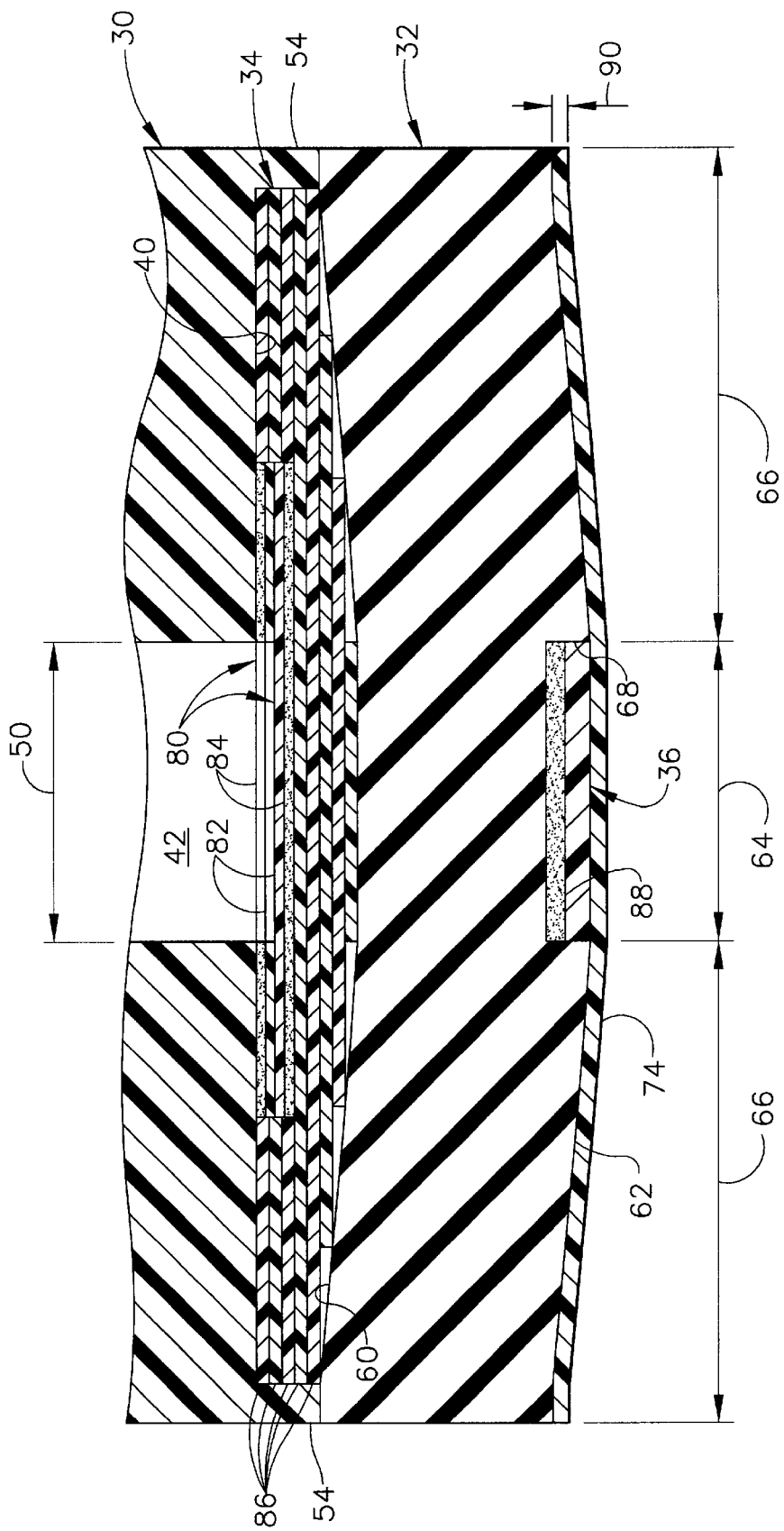
FIG. 5 is a cross section of the probe taken in the plane of line 5—5 of FIG. 2.

As shown in FIG. 2, the core 30 has an exterior surface 40 sized and shaped for receipt within the opening 14 of the component 16. As illustrated in FIG. 4, the core 30 has a centrally located slot 42 which intersects two lateral slots 44 which each intersect two longitudinal slots 46. In addition, a wedge-shaped opening 48 is provided above the central slot 42 for receiving the actuation rod 26. The slots 42, 44, 46 give a central portion 50 of the core 30 flexibility so the core can be moved between a retracted position (illustrated in FIG. 2) for inserting the probe 10 into and removing the probe from the opening 14 in the component 16 and an expanded position (illustrated in FIG. 3) in which the probe is sized and shaped for at least partially filling the opening and contacting the preselected surface 12 of the component for inspecting the surface. Although the central portion 50 of the core 30 may have other lengths without departing from the scope of the present invention, the central portion of the preferred embodiment has a length generally equal to the width of the eddy current array 36 as shown in FIG. 5. Although the core may be made of other materials without departing from the scope of the present invention, the core 30 of the preferred embodiment is molded from semi-rigid polyurethane. As further illustrated in FIG. 4, the core 30 may include threaded inserts 52 for attaching the core to the support 22. As illustrated in FIG. 5, end margins 54 of the core 30 protrude outward from the exterior surface 40 of the core and are attached to the covering 32 to prevent the covering from becoming detached from and sliding over the core 30 due to shearing forces as the probe 10 is inserted in the opening 14.

The covering 32 is positioned over the exterior surface 40 of the core 30 such that an inner face 60 of the covering faces the core. The covering 32 also has an outer face 62 opposite the inner face 60. The outer face 62 has a central portion 64 and opposite end portions 66 extending longitudinally outward from the central portion. As illustrated in FIG. 5, a groove 68 is provided in the central portion 64 of the outer face 62 for receiving the eddy current array 36. As illustrated in FIG. 2, the inner face 60 of the covering 32 includes longitudinal ribs 70 separated by longitudinal slots 72. Although the covering may be made of other materials without departing from the scope of the present invention, the covering 32 of the preferred embodiment is molded from polyurethane.

The eddy current array 36 is positioned over the central portion 64 and within the groove 68 in the outer face 62 of the covering 32. The array 36 is adhesively bonded to the bottom of the groove 68 in the covering 32. The array 36, which is conventional, generates and detects magnetic fields in the component 16 to inspect the preselected surface 12 of the component. The eddy current array 36 has an outer surface shaped substantially identically to the preselected surface 12 of the component 16 when the core 30 is in the expanded position for contacting the probe 10 with the preselected surface of the component. A sacrificial sheet of protective material 74 having a low coefficient of friction (e.g, a polytetrafluoroethylene sheet) is adhesively bonded to the outer surface of the array 36 and the outer face 62 of the covering 32 to permit the probe 10 to easily slide across the preselected surface 14 of the component 16 as it is inserted in the opening 12 and removed from the opening. Although the sheet 74 may be made of other materials without departing from the scope of the present invention, the sheet of the preferred embodiment is Teflon® polytetrafluoroethylene tape having a nominal thickness of about 0.0045 inches. Teflon® is a federally registered trademark of E.I. du Pont de Nemours and Company of Wilmington, Del.

As further illustrated in FIG. 5, the element 34 is positioned between the exterior surface 40 of the core 30 and the inner face 60 of the covering 32. The element 34 has a laminated construction formed by a plurality of layers of sheet material. Two of the layers, generally designated by 80, have a coefficient of friction selected to permit the inner face 60 of the covering 32 to move tangentially with respect to the exterior surface 40 of the core 30 as the actuation rod 26 moves the core from the retracted position to the expanded position. In other words, these two layers 80 are slick so they permit the covering 32 to slide with respect to the core 30 so the covering does not distort from its intended shape as the core expands into the opening 14 of the component 16. This ensures intimate contact between the probe 10 and the preselected surface 12 of the component 16 being inspected. Although the two layers 80 may be made of other materials without departing from the scope of the present invention, the layers of the preferred embodiment are Teflon® polytetrafluoroethylene tape having a nominal thickness of about 0.0045 inches. Each layer of tape comprises a flexible sheet of polytetrafluoroethylene 82 and an adhesive layer 84. One adhesive layer 84 bonds the respective sheet 82 to the exterior surface 40 of the core 30, and the other adhesive layer bonds the respective sheet to the inner face 60 of the covering 32. Thus, the polytetrafluoroethylene sheets 82 face one another so the sheets are free to move tangentially with respect each other.

The element 34 also includes several probe shaping layers of compressibly resilient material 86. As illustrated in FIG. 5, more layers of material 86 underlie the central portion 64 of the cover 32 than underlie the opposite end portions 66 of the covering. As a result, the central portion of the element 34 is thicker than the end portions and the central portion of the outer face 60 of the covering 32 and the array 36 are raised above the end portions of the outer face of the covering. This ensures a tight fit between the array 36 and the surface 12 being inspected but tapers the exterior surface 40 of the cover for easing insertion of the central portion of the covering and the array into the opening. Although the layers of compressibly resilient material 86 may be made of other materials without departing from the scope of the present invention, the layers of the preferred embodiment are made of Kapton® tape having a nominal thickness of about 0.003 inches. Kapton® is a federally registered trademark of E.I. du Pont de Nemours and Company. The adhesive layer of the Kapton® tape provides the layered element 34 with its compressible resilience.

To assemble the probe 10, the core 30 is cast in the shape shown in FIG. 4. The first layer 80 is bonded to the core 30, and slit along lines corresponding to the slots 42, 44, 46 in the core 30. Three probe shaping layers 86 are applied to each end of the core 30 adjacent the first layer 80. The second layer 80 is applied face-to-face over the first layer and held in place while the fourth probe shaping layer 86 is applied. The remaining layers 86 are applied to achieve the desired profile of the probe 10 as shown in FIG. 5. The ribbed covering 32 is positioned over and bonded to the layers 86. The end margins 54 of the core 30 are cast in place by applying a limited amount of polyurethane material over the ends of the layers 86 and allowing it to cure. A limited amount of polyurethane material is used to fill the end margins 54 to prevent it from filling the slots 72 between the ribs 70 in the covering 30 in the area over the layers 80. The array 36 is bonded in the slot 42 of the covering using transfer tape 88, and the sheet of material 74 is applied to the outer face 62 of the covering 32. Preferably, the probe 10 is constructed so that when the core 30 is in the retracted position, the outer surface of the sheet of protective material 32 is sized and shaped substantially identically to a nominal opening 14 for which the probe is made. Thus, when the core 30 is moved to the expanded position, the eddy current array 36 is maintained at a preselected distance 90 from the surface 12 of the component 16. Once assembled, the probe 10 may be used in a conventional manner.

When introducing elements of the present invention or the preferred embodiment(s) thereof, the articles "a", "an", "the" and "said" are intended to mean that there are one or more of the elements The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An eddy current inspection probe for inspecting a preselected surface at least partially defining an opening in a component, said eddy current inspection probe comprising:
    a core having an exterior surface sized and shaped for receipt within the opening of the component, the core being moveable between a retracted position for inserting the probe into and removing the probe from the opening in the component and an expanded position in which the probe is sized and shaped for at least partially filling the opening and contacting the preselected surface of the component for inspecting the surface;
    a compliant covering positioned over the exterior surface of the core having an inner face facing the core and an outer face opposite the inner face;
    an eddy current array positioned over the outer face of the covering for generating and detecting magnetic fields in the component to inspect the preselected surface of the component, the eddy current array having an outer surface shaped substantially identically to the preselected surface of the component when the core is in the expanded position for maintaining the outer surface of the array a preselected distance from the surface of the component; and
    an element positioned between the exterior surface of the core and the inner face of the covering having a coefficient of friction selected to permit the inner face of the covering to move tangentially with respect to the exterior surface of the core as the core is moved from the retracted position to the expanded position to ensure intimate contact between the probe and the preselected surface of the component being inspected.

2. A probe as set forth in claim 1 wherein the element comprises a flexible sheet having a first side adhesively bonded to one of the exterior surface of the core and the inner face of the covering, and a second side opposite said first side having the coefficient of friction selected to permit the inner face of the covering to move tangentially with respect to the exterior surface of the core.

3. A probe as set forth in claim 2 wherein:
    said flexible sheet is a first sheet having said first side bonded to the exterior surface of the core; and
    the element further comprises a second flexible sheet having a first side adhesively bonded to the inner face of the covering, and a second side opposite its first side facing said first flexible sheet and having the coefficient of friction selected to permit the inner face of the covering to move tangentially with respect to the exterior surface of the core.

4. A probe as set forth in claim 3 wherein each of said first and second sheets includes a layer of polytetrafluoroethylene.

5. A probe as set forth in claim 1 wherein a portion of the inner face of the covering is attached to the core to prevent the covering from separating entirely from the core.

6. A probe as set forth in claim 1 wherein:
    the outer face of the covering has a central portion and opposite end portions extending longitudinally outward from the central portion;
    the eddy current array is positioned over the central portion of the outer face of the covering; and
    the element positioned between the exterior surface of the core and the inner face of the covering is layered, the element has a central portion underlying the central portion of the cover and opposite end portions extending longitudinally outward from the central portion of the element and underlying the respective end portions of the covering, and the central portion of the element has a first thickness and each of the end portions of the element has a second thickness less than said first thickness so the central portion of the outer face of the covering and the array are raised above the end portions of the outer face of the covering for easing insertion of the central portion of the covering and the array into the opening.

7. An eddy current inspection probe for inspecting a preselected surface at least partially defining an opening in a component, said eddy current inspection probe comprising:
    a core having an exterior surface sized and shaped for receipt within the opening of the component;
    a compliant covering positioned over the exterior surface of the core having an inner face facing the core and an outer face opposite the inner face, the outer face of the covering having a central portion and opposite end portions extending longitudinally outward from the central portion;
    an eddy current array positioned over the central portion of the outer face of the covering for generating and detecting magnetic fields in the component to inspect the preselected surface of the component, the eddy current array having an outer surface shaped substantially identically to the preselected surface of the component for contacting the probe with the preselected surface of the component; and a layered element positioned between the exterior surface of the core and the inner face of the covering, the element having a central portion underlying the central portion of the cover and opposite end portions extending longitudinally outward from the central portion of the element and underlying the respective end portions of the covering, the central portion of the element having a first thickness and each of the end portions of the element having a second thickness less than said first thickness so the central portion of the outer face of the covering and the array are raised above the end portions of the outer face of the covering for easing insertion of the central portion of the covering and the array into the opening and ensuring intimate contact between the probe and the preselected surface of the component being inspected.

8. A probe as set forth in claim 7 wherein the layered element comprises a plurality of sheets stacked face-to-face.

9. A probe as set forth in claim 8 wherein the layered element further comprises a resiliently compressible adhesive layer positioned between adjacent sheets of said plurality of sheets.

* * * * *